(12) United States Patent
Choe et al.

(10) Patent No.: US 8,611,980 B2
(45) Date of Patent: Dec. 17, 2013

(54) ELECTROCARDIOGRAPH MONITORING DEVICE AND CONNECTOR

(71) Applicant: Cardiac Lead Technologies, LLC, Bethesda, MD (US)

(72) Inventors: William Choe, Highlands Ranch, CO (US); Paul Ruzumna, Glencoe, IL (US)

(73) Assignee: Cardiac Lead Technologies, LLC, Bethesda, MD (US)

( * ) Notice: Subject to any disclaimer, the term of this patent is extended or adjusted under 35 U.S.C. 154(b) by 0 days.

(21) Appl. No.: 13/770,614

(22) Filed: Feb. 19, 2013

(65) Prior Publication Data

US 2013/0231546 A1    Sep. 5, 2013

Related U.S. Application Data

(62) Division of application No. 12/149,733, filed on May 7, 2008.

(60) Provisional application No. 60/916,523, filed on May 7, 2007.

(51) Int. Cl.
*A61B 5/0408* (2006.01)
*A61B 5/0416* (2006.01)

(52) U.S. Cl.
USPC ............................ 600/391; 600/392; 600/393

(58) Field of Classification Search
USPC .................................................. 600/391–393
See application file for complete search history.

(56) References Cited

U.S. PATENT DOCUMENTS

| | | | |
|---|---|---|---|
| 2,943,628 A * | 7/1960 | Howell | 600/391 |
| 3,311,111 A | 3/1967 | Bowers | |
| 3,380,445 A | 4/1968 | Frasier | |
| 4,033,333 A | 7/1977 | DeSalvo et al. | |
| 4,049,004 A | 9/1977 | Walters | |
| 4,082,086 A | 4/1978 | Page et al. | |
| 4,090,752 A * | 5/1978 | Long | 312/42 |

(Continued)

FOREIGN PATENT DOCUMENTS

WO   WO-2008-068695 A1   6/2008

OTHER PUBLICATIONS

European Search Report issued in Application No. 10802858.0 dated Dec. 6, 2012.

(Continued)

*Primary Examiner* — Lee S Cohen
(74) *Attorney, Agent, or Firm* — Venable LLP; Henry J. Daley

(57) ABSTRACT

The present invention relates to electrocardiography and to electrode arrangements used in electrocardiographic monitoring devices. An EKG patch may include a plurality of individual EKG patches, each comprising a base layer and a plurality of electrodes capable of receiving an electrical signal generated by the myocardium of a human heart. Each of the plurality of the individual EKG patches may be stacked on top of each other such that each electrode in an individual patch aligns and contacts with at least one corresponding electrode in an adjacent EKG patch, thereby allowing a free flow of electricity through the plurality of stacked EKG patches, and such that the bottom-most EKG patch may be contacted with the skin of a patient. A temporary or release adhesive may be placed between each of the plurality of EKG patches such that the bottom-most EKG patch may be peeled away from the stack after each use.

12 Claims, 14 Drawing Sheets

(56) References Cited

U.S. PATENT DOCUMENTS

| | | |
|---|---|---|
| 4,209,020 A | 6/1980 | Nielsen |
| 4,233,987 A | 11/1980 | Feingold |
| 4,331,153 A | 5/1982 | Healy |
| 4,354,509 A | 10/1982 | Strahwald |
| 4,365,634 A | 12/1982 | Bare |
| 4,516,581 A | 5/1985 | Sessions |
| 4,583,549 A | 4/1986 | Manoli |
| 4,852,572 A | 8/1989 | Nakahashi |
| 4,957,109 A | 9/1990 | Groeger |
| 5,042,481 A | 8/1991 | Suzuki |
| 5,184,620 A | 2/1993 | Cudahu et al. |
| 5,507,290 A | 4/1996 | Kelly |
| 5,634,468 A | 6/1997 | Platt et al. |
| 5,697,369 A | 12/1997 | Long |
| 5,782,238 A | 7/1998 | Beitler |
| 5,785,040 A | 7/1998 | Axelgaard |
| 5,868,671 A | 2/1999 | Mahoney |
| 5,916,159 A | 6/1999 | Kelly et al. |
| 5,947,897 A | 9/1999 | Otake |
| 6,032,063 A | 2/2000 | Hoar |
| 6,201,981 B1 | 3/2001 | Yarita |
| 6,205,346 B1 | 3/2001 | Akiva |
| 6,219,569 B1 | 4/2001 | Kelly |
| 6,360,119 B1 | 3/2002 | Roberts |
| 6,408,200 B1 | 6/2002 | Takashina |
| 6,453,186 B1 | 9/2002 | Lovejoy |
| 6,532,379 B2 | 3/2003 | Stratbucker |
| 6,546,285 B1 | 4/2003 | Owen |
| 6,560,473 B2 | 5/2003 | Dominguez |
| 6,636,754 B1 | 10/2003 | Baura |
| 7,206,630 B1 | 4/2007 | Tarler |
| 7,215,989 B1 | 5/2007 | Burks |
| 7,860,546 B2 * | 12/2010 | Coggins ............... 600/391 |
| 2002/0091413 A1 | 7/2002 | Cappa et al. |
| 2006/0047215 A1 | 3/2006 | Newman |
| 2006/0276715 A1 | 12/2006 | Yeo |
| 2007/0060993 A1 | 3/2007 | Craige |
| 2007/0073132 A1 | 3/2007 | Vosch |
| 2008/0027513 A1 | 1/2008 | Carbunaru |
| 2009/0177073 A1 | 7/2009 | Sonnenborg |
| 2010/0234746 A1 | 9/2010 | Sebelius |

OTHER PUBLICATIONS

Janata, et al.; *Quality of ECG Monitoring with a Miniature ECG Recorder*, from the Dept. of Emergency Medicine, Jun. 2008 (vol. 31; 9 pgs).

\* cited by examiner

ELECTROCARDIOGRAPH MONITORING DEVICE AND CONNECTOR

CROSS-REFERENCE TO RELATED APPLICATION

This application is a divisional application of U.S. application Ser. No. 12/149,733, filed May 7, 2008, entitled "Electrocardiograph Monitoring Device and Connector," which claims priority to U.S. Provisional Application No. 60/916,523 filed May 7, 2007. The entire contents of both of the foregoing applications are hereby incorporated by reference.

BACKGROUND

1. Field of Invention

This application relates to electrocardiograph devices, and more particularly to electrocardiograph patches, connectors and devices that include the patches and connectors.

2. Discussion of Related Art

Human cardiac muscle tissue operates through similar electric and electrochemical properties as human neurons and skeletal muscle, in that the human heart generates an electrical impulse that is propagated to the cardiac muscle, which becomes stimulated. Once the cardiac muscle is stimulated, it contracts. It is the ordered stimulation of the cardiac muscle, or myocardium, that causes the heart to contract, which then pumps blood throughout the human body. The electrical impulse, or electrical potential, that is generated by the heart appears throughout the body and on the surface of the body, and is thus capable of being read by electrodes placed on the surface of the human body. This has traditionally been done by placing a number of electrical leads, or electrodes, on the surface of a patient, which are capable of receiving the electrical potential generated by the heart and transmitting that information to one or more devices for recording. In order to properly assess and diagnose cardiac function, or injury, it is necessary to evaluate several electrodes at once. It is known to place electrodes on each of the four limbs of a patient in order to properly read and record the electrical potential. Three of these electrodes are placed on the patient's right and left arms, and left leg, with the fourth optionally placed on the right leg as a ground lead. It is also possible to shorten the distance between these leads while still maintaining the proper amplitude of signal to obtain a proper reading. In this instance, a modified three-lead system is employed in which electrodes are placed on the right shoulder, left shoulder, and mid-sternum areas. Three leads are sufficient in some instances to properly assess cardiac rhythm. In some cases, four leads may be suitable. In other cases, five or six leads may be suitable.

As can be appreciated, the placement of separate electrodes and the connection of the respective leads from those electrodes to a recording device can be inconvenient and time-consuming to hospital personnel. Placing the leads on the limbs of a patient as described above is a time consuming process and can cause a delay in treatment in an emergency situation. In an office setting, where the patient is fully clothed, placing electrodes in this manner may require the patient to remove his or her clothing, which makes the procedure more difficult for both patient and medical personnel.

Numerous devices have been created to read the electrical potential generated by the heart. Many of these devices are electrocardiographic monitoring devices which employ electrodes placed along the precordium and the limbs of a patient, while others are comprised of just leads placed on the precordium. Some devices include a large triangular patch, with electrodes embedded therein, designed to cover the bulk of the patent's chest. The large area covered by this patch allows for increased signal amplitude to allow for more accuracy in assessing the EKG complexes. Others employ smaller patches made of rigid materials housing an array of electrodes, and still others have been created for very specialized, limited fields and purposes, such as magnetic resonance imaging, thus limiting their use to a single application or method. All of these devices require the chest of the patient to be exposed in order to ensure proper placement and may thus be improved upon.

Additionally, permanent implantable pacemakers and implantable cardioverter defibrillators are now common. In order for medical personnel to assess whether these devices are functioning properly, it is necessary to monitoring the patient's heart rhythm. While it is possible to use the three limb lead configuration to accomplish this task, typically the EKG monitors employed utilize a four lead cable, thus requiring the ground lead. Attaching each electrode and wire on the patient is a cumbersome process, and time consuming especially if that patient is fully clothed.

DETAILED DESCRIPTION

It is therefore an object of the present invention to provide improved electrocardiograph patches, connectors and/or devices that include the patches and connectors. In that regard, some embodiments of the present invention relate to electrocardiography (EKG) and to electrode arrangements used in electrocardiographic monitoring and recording. In some embodiments, the present invention is particularly related to a pad or patch containing a plurality of electrodes for placement upon a patient's chest that is sufficiently pliable so as to conform to the contours of the patient's chest. In these embodiments, the pad or patch is small, and the distance of the electrodes is substantially shortened from the standard EKG limb leads, allowing ease of use while still being able to obtain a suitable signal. In that regard, the pad or patch can be centrally placed at the top of the chest just below the suprasternal notch, thereby eliminating the need for disrobing. In other embodiments of the present invention, a connector is provided which allows for fast and simple connection between the pad or patch containing said electrodes and the devices and equipment typically used to monitor and view electrocardiographic information. Embodiments of the present invention may be used to passively and non-invasively monitor or record the heart's electrical activity from the surface of a patient's chest, and where desired, the records derived from use of embodiments of the present invention may be correlated with standard EKG limb leads (e.g. leads I, II and III).

While not portending to be limited in any manner, the following U.S. patents are incorporated herein by reference with respect to their disclosure: U.S. Pat. No. 3,380,445 to Frasier; U.S. Pat. No. 4,033,333 to DeSalvo et al.; U.S. Pat. No. 4,082,086 to Page et al.; U.S. Pat. No. 4,233,987 to Feingold; U.S. Pat. No. 4,331,153 to Healy; U.S. Pat. No. 4,516,581 to Sessions; U.S. Pat. No. 4,583,549 to Manoli; U.S. Pat. No. 5,782,238 to Beitler; U.S. Pat. No. 6,360,119 to Roberts; and U.S. Pat. No. 6,408,200 to Takashina.

Figure 1:
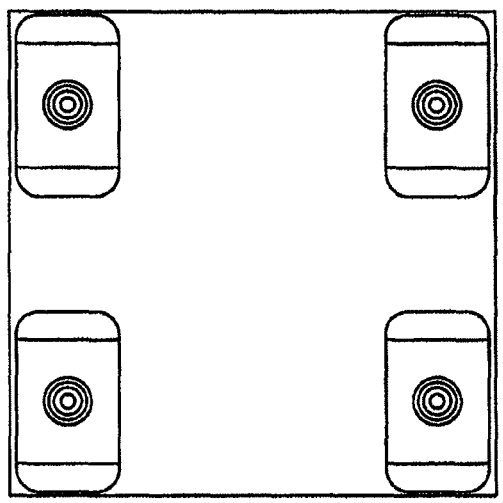
FIG. 1 is a top perspective view of a multi-lead EKG patch, in accordance with at least some embodiments of the present invention.
Figure 2:
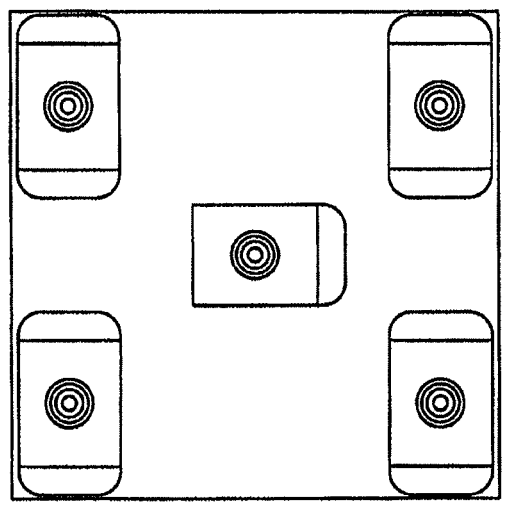
FIG. 2 is a top perspective view of another multi-lead EKG patch, in accordance with at least some embodiments of the present invention.

FIGS. 1 and 2 show EKG monitoring patches in accordance with a couple of embodiments of the present invention. In the depicted embodiments, the device is configured so that the sides that are not visible in FIGS. 1 and 2 are placed in direct contact with the skin of a patient and attached thereto via any number of standard means including, without limitation, straps or similar physical restraints, biocompatible adhesives, electrode gel, or similar means. In some embodiments of the current invention, the EKG patch comprises: (a) a base layer that has a base surface that makes contact with the skin of the patient and attaches to the patient substantially as described herein; and (b) a plurality of electrodes for monitoring the electrical potential generated by the heart of the wearer of the depicted device. The EKG patch can include a second layer, or even multiple layers, that that may cover or be attached to the plurality of electrodes in some embodiments. The plurality of electrodes can be three, four, five or six electrodes, for example, in some embodiments of the current invention. However, broad concepts of the current invention are not limited to only these specific numbers of electrodes. FIG. 1 shows an example of an EKG patch that has four electrodes according to an embodiment of the current invention. FIG. 2 shows an example of an EKG patch that has five electrodes according to an embodiment of the current invention. In some embodiments of the current invention, the EKG patch further comprises a removable film layer in contact with the skin-contacting surface of the base layer that protects the skin-contacting surface and prevents its exposure to contaminants or items that may damage the surface and impede contact with the patient.

Figure 2A:
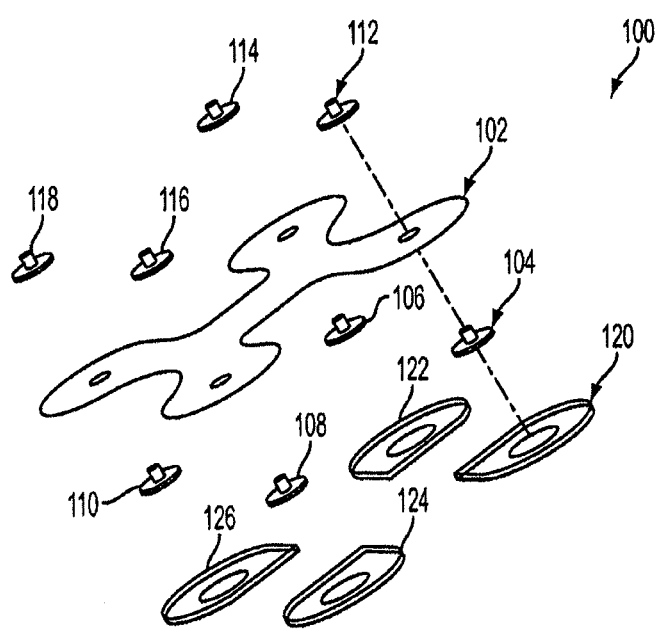
FIG. 2A is an exploded perspective view of another multi-lead EKG patch, in accordance with some embodiments of the present invention.
Figure 2B:
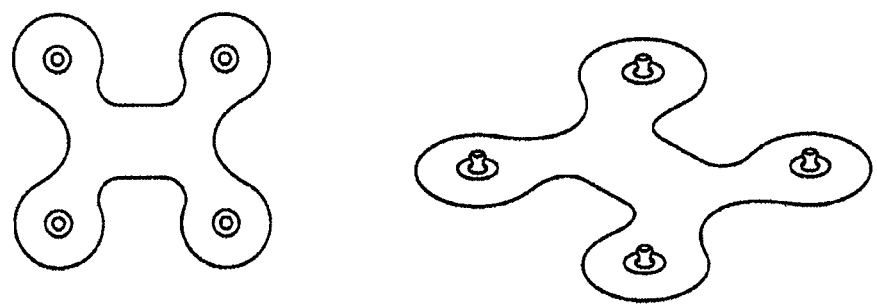
FIG. 2B shows a top, side and perspective view of the EKG patch of FIG. 2A in an assembled configuration.

FIG. 2A illustrates an EKG patch 100 in an exploded view according to an embodiment of the current invention. The EKG patch comprises a base layer 102 and a plurality of electrodes 104, 106, 108 and 110. The plurality of electrodes 104, 106, 108 and 110 can be held in a fixed configuration with respect to the base layer 102, for example by corresponding snaps 112, 114, 116 and 118. Although this embodiment has four electrodes 104, 106, 108 and 110, the invention is not limited to embodiments with four electrodes. Furthermore, the snaps are suitable to hold the electrodes in a fixed configuration with respect to the base layer in some embodiments, but the invention is not limited to only this embodiment. The EKG patch may further include layers of hydrogel 120, 122, 124 and 126 over corresponding electrodes and adjacent regions of the EKG patch 100 in some embodiments of the current invention. The base layer 102 may also include a layer of adhesive material in some embodiments of the current invention. Alternatively, the hydrogel can also provide an adhesion layer in some embodiments. The shape of the EKG patch can be selected to facilitate proper placement, attachment and removal in some embodiments. For example, the shape depicted for the embodiment of the EKG patch 100 may allow the user to easily remove the EKG patch 100 by lifting one or more of the flaps proximate the electrodes. The snaps 112, 114, 116 and 118 can provide suitable electrical connectors to connect the corresponding electrodes 104, 106, 108 and 110 to an EKG monitoring system. In some embodiments of the current invention, all of the materials of the EKG patch can be selected to be non-magnetic materials so that the EKG patch can be used in environments with magnetic fields. For example, the EKG patch 100 may be constructed of non-magnetic materials so that the EKG patch can be used in conjunction with MRI systems. In some embodiments, the EKG patch can have perforations in the base layer 102 so that one or more of the electrodes 104, 106, 108 and 110 can be separated from the remaining electrodes. FIG. 2B shows top, side and perspective views of the EKG patch 100 according to an embodiment of the current invention in an assembled configuration with some of the dimensions for this example listed in inches.

The connector elements may be any number of configurations capable of creating an electrical connection between the electrode and the lead wire, such as metal snaps, clamps, and similar means of connection. The electrodes are made of an electrically conductive material capable of receiving the electrical potential generated by the patient's heart and transmitting that potential as a signal along its length to any one or more of the devices and/or equipment that can be used to monitor and view electrocardiographic information. The electrodes can also contain a substance in some embodiments of the current invention that will facilitate the attachment of the patch to the patient, though that is not necessary. In operation, the location of the patch can be selected as described hereinbelow and the film layer is removed, exposing the surface of the device that will make contact with the patient's skin and also exposing the electrodes, so that they may be placed directly against the patient's skin and receive the strongest possible signal. The patch is then contacted with the patient's skin and secured in place as stated hereinabove. The electrodes can then be connected to the lead wires, which are also connected to the EKG monitoring equipment, and electrical signals from the patient are captured and read.

The depicted embodiment is not limited in the number of electrodes that can be present, and is sufficiently scalable so as to contain any number of electrodes desired, so long as the electrodes are capable of fitting within the device itself while maintaining the medically relevant distance between them. In an embodiment, EKG patches can be configured in sizes ranging from about 3 cm×3 cm) square to about 16 cm×16 cm square in some embodiments of the current invention. For example, EKG patches about 3×3 inches (about 8 cm×8 cm) square have been found to work well in some applications. The EKG patches may be of any shape that will facilitate the monitoring of a patient's electrical potential, such as a rectangle, a cloverleaf configuration, a triangle, an oval, a circle, etc. In another embodiment, the EKG patch includes a series of perforations which can allow medical personnel to detach one or more of the individual electrodes so they can be placed at different locations. For example, in some cases it may be desirable to separate one or more electrodes from the remaining electrodes of the EKG patch in order to place the patch around a wound. In other cases, it may allow the user to adjust the arrangement of the electrodes in order to optimize the detected signal in that particular case. These are just a couple of examples of the potential usefulness of providing an EKG patch in which one or more electrodes can be separated from the remaining electrodes of the EKG patch. This aspect of the current invention is not limited to only these particular examples. In some embodiments, the device can be disposable so as to be as clean and sanitary as possible with each use. In some embodiments, the EKG patch is not rigid, but rather sufficiently flexible so as to be able to conform to the contours of the human body. In that regard, the EKG patch may be made of rubber, flexible plastic, silicone, cloth, or other silastic materials capable of conforming its shape to the contours of the human body.

Figure 3:
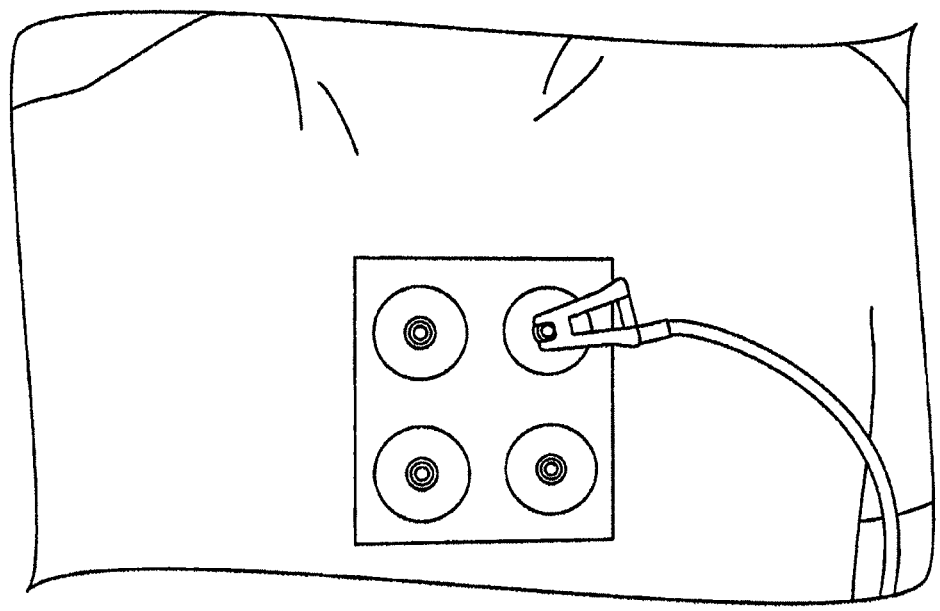
FIG. 3 is a perspective view of a multi-lead EKG patch, in accordance with at least some embodiments of the present invention, affixed to the chest of a patient with a single lead wire connected.
Figure 3A:
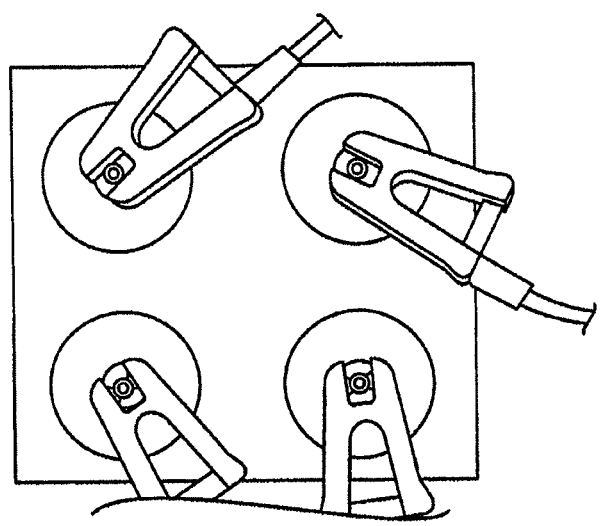
FIG. 3A is a close-up perspective view of the multi-lead EKG patch of FIG. 3, showing four individual lead wires connected.

FIG. 3 show an example of the placement of an EKG patch on a patient according to at least some embodiments of the present invention. Such a placement was found to work well with at least some embodiments of EKG patches according to the current invention. In this example, the EKG patch is placed along the midline of the sternum, approximately 2 to 4 cm below the suprasternal notch, a location that roughly corresponds to intercostal space one, two or three. Notwithstanding the foregoing, other locations may be suitable for use with the EKG patch of the present invention and the presently described placement is not intended to be limiting in any manner. A depiction of the connection of the electrodes of an EKG patch to the lead wires in accordance with at least some embodiments of the present invention is presented are illustrated in FIG. 3A. Each electrode can be individually connected to the monitor in numerous ways including, without limitation, via lead wires which are individually connected to each electrode on the EKG patch, or by way of a single cable with individual lead wires that separate from the cable at the patch, not before. As shown in FIG. 3A, one of the means by which the lead wires may be connected to the EKG patch is by alligator-type clips, though it is intended that the electrodes can be connected to the lead wires by any one or more available approaches, such as snap connectors, clips, wires, and other means.

Figure 4:
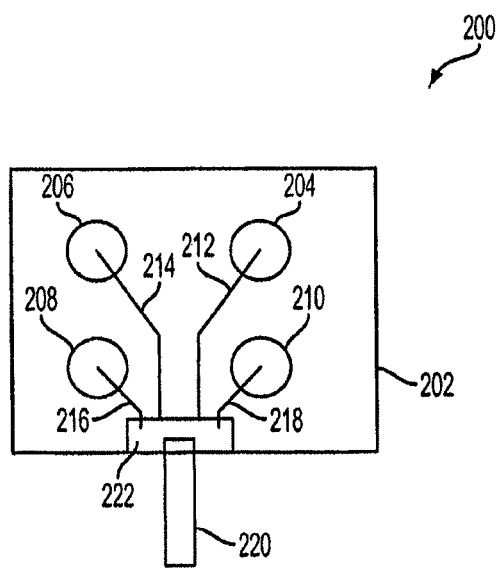
FIG. 4 is a close-up perspective view of a multi-lead EKG patch, in accordance with at least some embodiments of the present invention, showing a single multi-wire cable connection attached to each of four individual electrodes.

FIG. 4 shows an EKG patch 200 according to another embodiment of the present invention. In this embodiment, the EKG patch 200 comprises a base layer 202 and a plurality of electrodes 204, 206, 208 and 210. Again, the number of electrodes is show as an example, and not as a limitation. In this embodiment, each electrode has pre-wired electrical connections 212, 214, 216 and 218 for each of the corresponding electrodes 204, 206, 208 and 210. The EKG patch 200 can provide an EKG patch that can be easily connected to a single cable 220 through a cable connector 222. This cable 220 can then be attached to an EKG monitor. This embodiment can confer a substantial advantage in some applications over the prior art in that only a single point of connection need be made to the device in order for it to operate. Prewired EKG, patches such as EKG patch 200, can include a layer of material covering the wires such as 212, 214, 216 and 218 in some embodiments. Furthermore, the base layers in the various embodiments of the current invention can be single layers of multiple layers of material without departing from the general concepts of the current invention.

Figure 5:
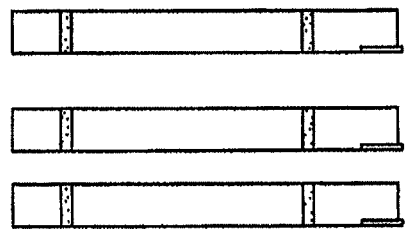
FIG. 5 is a block diagram side view of a plurality of multi-lead EKG patches shown stacked on top of each other, in accordance with at least some embodiments of the present invention.

FIG. 5 shows another embodiment of an EKG patch according to at least some aspects of the present invention. In this embodiment, a plurality of EKG patches are presented and packaged as a stacked unit, similar to a note pad, with each patch stacked on top of the prior patch. In this embodiment, as each EKG patch is used a single time, it is peeled away from the bottom of the stack and discarded, leaving a new patch for subsequent use. This process can continue until such time as all of the EKG patches have been used from the stack. The patches may be held together with a layer of a temporary or release adhesive that is placed in between each of the patches that is sufficiently strong so as to hold the layers of patches together, but which also allows the user to peel the used EKG patch away after use. As is shown in FIG. 5, the temporary or release adhesive does not have to cover the entire surface of each patch, but may rather be placed on each patch at one or more discrete locations to facilitate removal. Importantly, the electrically active area on the electrodes for each patch would be exposed and allowed to contact the electrodes from the other layers, thereby allowing the electric potential generated by the patient's heart to pass through the entire stack of patches. The patch located at the top of the stack would thus serve as the point of connection to the medical equipment for the entirety of the stack, as the proper amount of electrical connectivity would exist throughout the stack. The exposed bottom layer would touch the skin of the individual.

FIGS. 6-10 show an EKG connector in accordance with at least some embodiments of the present invention. This connector serves as a means by which an EKG patch can be connected to the monitoring medical equipment. In this regard, the EKG connector can serve the same purpose as the second layer of the EKG patch of the present invention, as it would provide the necessary electrical connectivity to the equipment, but would not make contact with the patient's skin. In some embodiments, in addition to the second layer, the EKG connector would include the third layer located under the second layer, which would become sandwiched between the second layer and the base layer upon connection to the EKG patch. The EKG patch would attach to the EKG connector and is made to allow simple connection between the disposable EKG patch and the cable. The EKG connector would be firm yet flexible to allow it to mold to the contours of the body, in a similar manner as the EKG patch.

Figure 8:
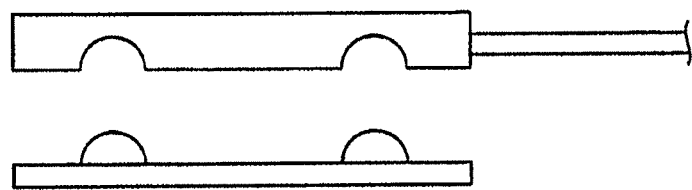
FIG. 8 is a block diagram side view of an EKG patch and an EKG patch connector, in accordance with at least some embodiments of the present invention.
Figure 9:
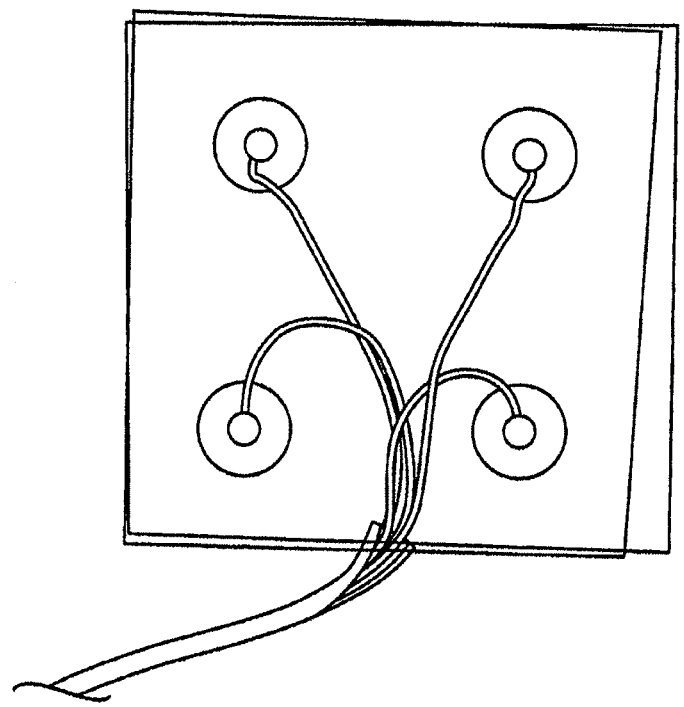
FIG. 9 is a top perspective view an EKG patch connector, in accordance with at least some embodiments of the present invention, showing a single multi-wire cable connection attached to each of four individual electrodes.
Figure 10:
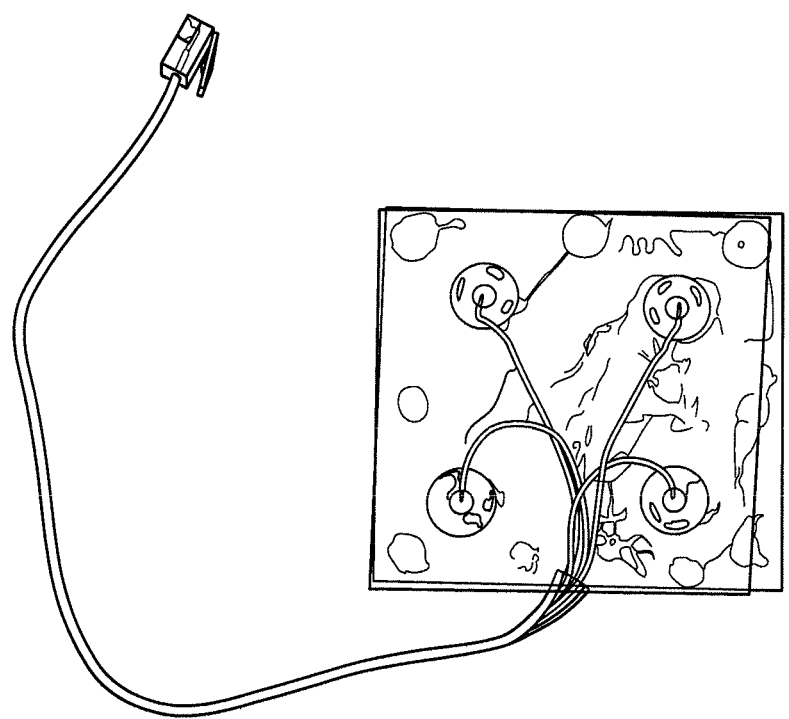
FIG. 10 is a top perspective view another EKG patch connector, in accordance with at least some embodiments of the present invention, showing a single multi-wire cable connection attached to each of four individual electrodes.

As shown in FIG. 8, the electrodes of an EKG patch are configured to be complimentary to the electrode housing of the EKG connector, thus allowing for ease of use and for the creation of a strong electrical connection between the electrodes of the EKG patch and the electrodes of the EKG connector. In this regard, the EKG connector can be a non-disposable, reusable device and the EKG patch used with it may be the only disposable portion of the device of the present invention, thereby helping to reduce waste. Many EKG devices currently known require that each electrode be connected to an individual lead wire separately, which can cause delays in treatment in emergency situations. The EKG connector according to some embodiments of the present invention can confer a substantial advantage over the prior art in that it can serve to connect an EKG patch to the monitoring equipment in a single step.

The EKG connector would have a base lower layer with a plurality of electrodes to match the number and location of the electrodes in the desired EKG patch. A second sheet would have wires connecting the multiple electrodes to a single cable which would exit the EKG connector and would then allow connection to the EKG monitor. In the presently preferred embodiment, the EKG patch and the EKG connector become attached via snap electrodes (FIG. 8), though they may also be attached together via the use of an adhesive, magnets, in a slotted area on the undersurface of the EKG connector where it can be inserted, or other means of connection known to those of skill in the art. Additionally, the cable extending from the EKG connector can be made detachable partway along its length with a male and female connection, allowing for ease of use, or it may be wireless. If it is wireless, a transmitter can be located on the EKG connector capable of receiving and transmitting a signal of the patient's electrical potential to a receiver located in the medical monitoring equipment.

There is disclosed a disposable ECG monitoring device for attachment to the skin of an individual, which device includes a plurality of electrodes for monitoring bio-skin potential disposed at suitable locations on a base or substrate. This device has a plurality of electrodes at a specified distance between the electrodes. It would be used at a specific location on the individual, specifically midline, 2 cm below the suprasternal notch. The electrodes would be connected to the monitor via individual snaps or via single connector and cable. A number of electrodes are attached to the second sheet by an adhesive coating, with the connector elements of the respective electrodes in place in the openings and secured to lead wires for attachment to monitoring apparatus. The individual electrodes include an adhesive base surface that can be exposed upon removal of a cover structure which normally overlies a pre-gelled pad and said base surface. The adhesively coated base surfaces of the electrodes are used to affix the device to the patient.

Figure 11:
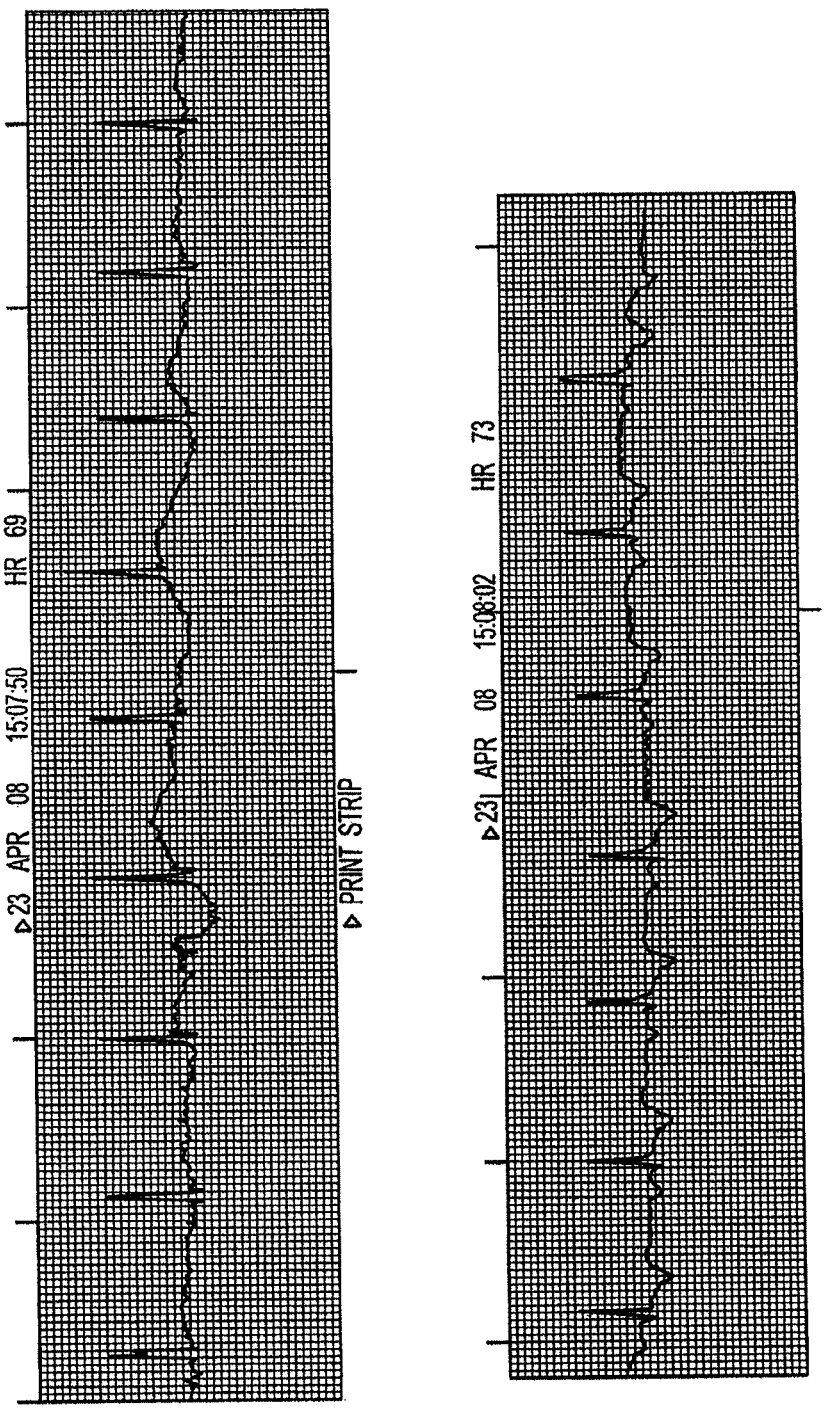
FIG. 11 shows traces taken from a conventional EKG system that has several separate leads attached at widely spaced positions on the patient's body.
Figure 12:
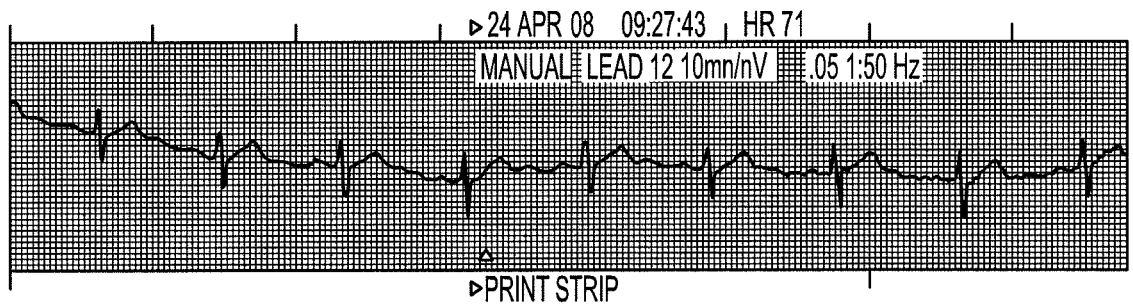
FIG. 12 show traces from an EKG system according to an embodiment of the current invention.
Figure 12:
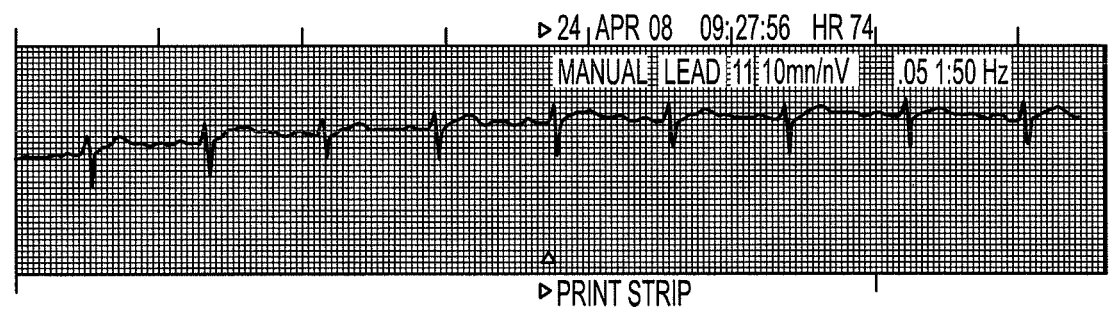
Figure 12:
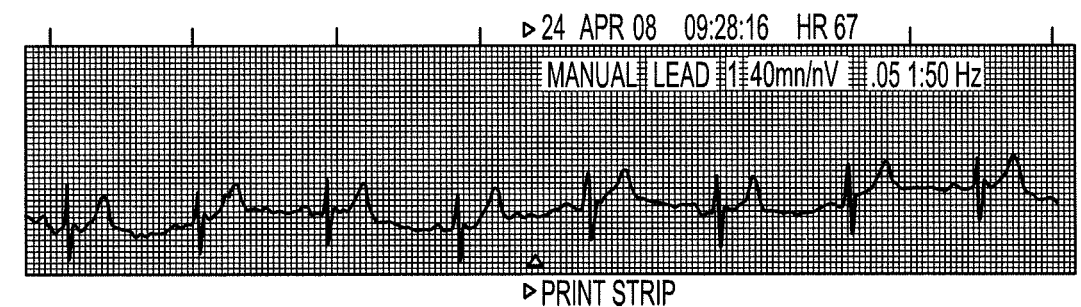

Currently when 3-5 lead telemetry EKG's are done, the electrodes are placed individually on the person's torso in a preconfigured design dating back to the early 1900's. The limitation of this is that it requires individual cables to connect to the separate electrode sites. Cables get tangled and it takes time to connect each electrode. In addition if one falls off, all of the tracings are affected. With our patch, up to 6 of the electrodes can be imbedded and there can be either individual snaps or a single connection will exit the patch. A reusable cable then would connect to the patch. A difference between this embodiment of the current invention and prior art reference U.S. Pat. No. 4,082,086 is that our patch works best when applied just under the suprasternal notch, midline on the person. The distances between each snap/electrode is a determined distance between 1.5 cm up to 15 cm apart. U.S. Pat. No. 4,082,086 does not specify the distances between the electrodes. FIG. 11 shows traces from a conventional EKG system that uses limb leads. FIG. 12 shows traces from an EKG system according to an embodiment of the current invention in which a single EKG patch has 4 electrodes that are spaced 1.5 cm apart. The overall dimension of the EKG patch in this example is 5.5 cm×5.5 cm. One can see from the example in FIG. 12, as compared to FIG. 11, that the EKG system according to the current invention provides suitable telemetry data even though only a small, compact, single EKG patch is used rather than multiple separately and widely spaced leads as in FIG. 11.

There is disclosed a disposable EKG monitoring device (from hereforth will be referred to as EKG patch) for attachment to the skin of an individual, which device includes a plurality of electrodes for monitoring bio-skin potential disposed at suitable locations of the individual. (See, for example, FIGS. 1 and 2). This device has a plurality of electrodes at a specified distance between the electrodes. It would be used at a specific location on the individual, specifically midline along the sternum, approximately 2 cm below the suprasternal notch at around intercostal space one or two. (FIG. 3) Other locations may yet be identified and used if the potentials are deemed to be of suitable quality.

The individual patches include an adhesive base surface and electrode that can be exposed upon removal of a cover structure which normally overlies a pre-gelled patch and said base surface. This surface would be attached to the skin of the individual. This patch is made of flexible material allowing said patch to mold to the contours of the individual body. The adhesively coated base surfaces of the patch allow it to affix the device to the patient. There would be a nonadhesive layer which is removed prior to attaching to the patient for storage purposes. The electrodes will have an electrically conductive material which will adhere to the skin as well. Another embodiment of the EKG patch may include perforations allowing the individual electrodes to be detached and placed at a different location. Further, the EKG patches can be made from nonmagnetic materials in some embodiments of the current invention so that they can be used in the presence of strong magnetic fields, such as in conjunction with magnetic resonance imaging (MRI) systems.

A plurality of electrodes are attached to the second sheet by an adhesive coating, with the connector elements of the respective electrodes in place in the openings, such as snaps, and connected to lead wires for attachment to the EKG monitor. (FIGS. 1, 2)

The connection of the electrodes to the monitor can be done several ways. Each electrode can be individually connected to the monitor via wires which are individually connected to the EKG patch (FIG. 3) as it is done currently with snap female electrodes or alligator clips. Another embodiment could include an additional layer sandwiched between the top and bottom layer with the electrodes on the EKG patch pre-connected to wires which exit the EKG patch as a single cable. This cable can then be attached to the EKG monitor (FIG. 4).

Another embodiment may allow the EKG patches to be packaged as a stacked unit with multiple EKG patches similar to a note pad. They would be held together with an adhesive layer on a portion of the EKG patch which would allow each unit to separate and be disposed of after each use. The electrically active area where the electrodes are would be exposed and allowed to contact the electrodes from the other layers making the stack a long electrical connection. The top layer would be connected to the lead wires connecting to the EKG monitor. The exposed bottom layer would touch the skin of the individual. (FIG. 5)

Figure 6:
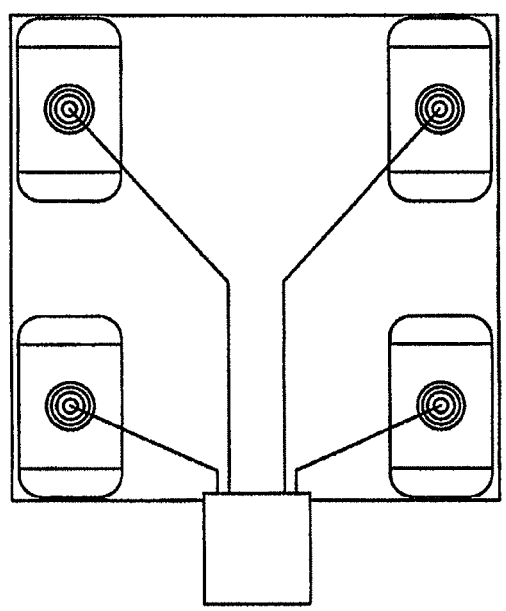
FIG. 6 is a block diagram top view of an EKG patch connector, in accordance with at least some embodiments of the present invention.
Figure 7:
FIG. 7 is a block diagram side view of the EKG patch connector shown in FIG. 6.

A second method to connect the EKG patch to the EKG monitor is via a nondisposable EKG monitoring device (from hereforth will be referred to as EKG connector). The EKG patch would attach to the EKG connector (FIGS. 6-10). This EKG connector is made to allow simple connection between the disposable EKG patch and the cable. The EKG connector would be firm yet flexible to allow it to mold to the contours of the body (FIGS. 6,7).

The electrodes of the EKG patch would fit into this EKG connector thus allowing for ease of use. Currently, each snap of the EKG sticker must be individually connected. The EKG connector would eliminate this step.

The EKG connector would have a base lower layer with a plurality of electrodes to match the number and location of the ones on the said EKG patch. A second sheet would have wires connecting the multiple electrodes to a single cable which would exit the EKG connector and would then allow connection to the EKG monitor. The EKG patch would attach to the EKG connector via snap electrodes (FIG. 8), via adhesive coating, magnetically, in a slotted area on the undersurface of the EKG connector where it can be inserted, or by yet undescribed method. In addition, the cable which will attach to the EKG monitor may be detachable partway along its length with a male and female connection allowing for ease of use, or wireless. If it is wireless, there would be a transmitter on the EKG connector and the EKG monitor would have a receiver.

The present invention, in various embodiments, includes components, methods, processes, systems and/or apparatuses substantially as depicted and described herein, including various embodiments, subcombinations, and subsets thereof. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments to facilitate a description of some concepts of the current invention. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included descriptions of one or more embodiments and certain variations and modifications, other variations and modifications are within the scope of the invention, e.g., as may be within the skill and knowledge of those in the art, based upon teachings of the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

We claim:

1. An EKG patch, comprising:
a plurality of individual EKG patches, each comprising a base layer and a plurality of electrodes capable of receiving an electrical signal generated by the myocardium of a human heart,
wherein each of the plurality of the individual EKG patches are stacked on top of each other such that each electrode in an individual patch aligns and contacts with at least one corresponding electrode in an adjacent EKG patch, thereby allowing a free flow of electricity through the plurality of stacked EKG patches, and such that a bottom-most EKG patch may be contacted with the skin of a patient, and
wherein a temporary or release adhesive is placed between each of the plurality of EKG patches such that the bottom-most EKG patch may be peeled away from the stack after each use.

2. The EKG patch according to claim 1, wherein, after each use, the bottom-most individual EKG patch is configured to be peeled away and discarded.

3. The EKG patch according to claim 1, wherein the temporary or release adhesive covers at least a portion of each individual EKG patch.

4. The EKG patch according to claim 1, wherein the electrodes of each individual EKG patch are exposed and contact the electrodes from each adjacent individual EKG patch, whereby electric potential generated by the patient's myocardium passes through the stacked plurality of EKG patches.

5. The EKG patch according to claim 1, wherein a top-most individual EKG patch is configured to be connected to an EKG monitoring system.

6. The EKG patch according to claim 1, wherein the plurality of electrodes on each individual EKG patch are spaced at least about 1.5 cm apart and less than about 15 cm apart.

7. The EKG patch according to claim 6, wherein the plurality of electrodes are spaced about 5.5 cm apart.

8. The EKG patch according to claim 1, wherein the plurality of electrodes comprise one of three, four, five or six electrodes.

9. The EKG patch according to claim 1, wherein dimensions of the EKG patch are within a range of about 3 cm×3 cm square to 16 cm×16 cm square.

10. The EKG patch according to claim 1, wherein the base layer comprises an adhesive material on a surface thereof for attaching the EKG patch to the patient.

11. The EKG patch according to claim 1, wherein said base layer has a shape suitable to facilitate at least one of positioning, attaching and removing said EKG patch from the patient.

12. The EKG patch according to claim 1, wherein the EKG patch is constructed from nonmagnetic materials such that the EKG patch is suitable for use in conjunction with magnetic fields.

* * * * *